(12) United States Patent
Emmert et al.

(10) Patent No.: US 7,987,701 B2
(45) Date of Patent: Aug. 2, 2011

(54) REAL-TIME, ON-LINE ANALYSIS FOR THE QUANTIFICATION OF TOTAL HALOACETIC ACID AND TRIHALOMETHANE SPECIES IN DRINKING WATER SUPPLIES

(75) Inventors: Gary Lynn Emmert, Collierville, TN (US); Michael Andrew Brown, Memphis, TN (US); Gija Geme, Warrensburg, MO (US); Paul Steven Simone, Jr., Bartlett, TN (US)

(73) Assignee: University of Memphis Research Foundation, Memphis, TN (US)

( * ) Notice: Subject to any disclaimer, the term of this patent is extended or adjusted under 35 U.S.C. 154(b) by 471 days.

(21) Appl. No.: 12/116,816

(22) Filed: May 7, 2008

(65) Prior Publication Data
US 2009/0277256 A1 Nov. 12, 2009

(51) Int. Cl.
*G01N 30/20* (2006.01)
(52) U.S. Cl. ...... 73/61.56; 73/61.52; 73/61.55; 73/61.59
(58) Field of Classification Search ............ 73/61.41, 73/61.43, 61.44, 61.52, 61.53, 61.55, 61.56, 73/61.58, 61.59
See application file for complete search history.

(56) References Cited

U.S. PATENT DOCUMENTS

| | | | |
|---|---|---|---|
| 5,358,557 A | 10/1994 | Jiang et al. | |
| 5,762,808 A | 6/1998 | Peyton | |
| 5,814,128 A | 9/1998 | Jiang et al. | |
| 5,858,792 A * | 1/1999 | Fanning et al. | 436/52 |
| 5,911,882 A | 6/1999 | Benjamin et al. | |
| 6,106,725 A | 8/2000 | Hong | |
| 6,408,227 B1 | 6/2002 | Singhvi et al. | |
| 6,499,362 B1 * | 12/2002 | Wolcott | 73/863.24 |
| 6,577,392 B1 * | 6/2003 | Nielsen et al. | 506/12 |
| 7,186,344 B2 | 3/2007 | Hughes | |
| 2004/0040841 A1 * | 3/2004 | Gonzalez-Martin et al. | 204/406 |
| 2007/0116601 A1 * | 5/2007 | Patton | 422/81 |
| 2008/0257019 A1 * | 10/2008 | Rosati et al. | 73/61.55 |
| 2008/0289397 A1 * | 11/2008 | Hassan et al. | 73/23.4 |

OTHER PUBLICATIONS

Measuring the concentrations of drinking water disinfection by-products using capillary membrane sampling-flow injection analysis, Water Research 39 (2005) 3827-3836, G. Geme et al.
On-line monitoring of µg/L levels of haloacetic acids using ion chromatography with post-column nicotinamide reaction and fluorescence detection, Analytica Chemica Acta 570 (2006) 259-266, P.S. Simone, Jr. et al.

* cited by examiner

*Primary Examiner* — David A. Rogers
(74) *Attorney, Agent, or Firm* — Wyatt, Tarrant & Combs, LLP; William S Parks

(57) ABSTRACT

Capillary membrane sampling-flow injection analyzer (CMS-FIA) analyses of drinking water samples for quantity measurements of total trihalomethane and haloacetic acid contaminants therein are provided. With the necessity to chlorinate drinking water to remove harmful bacteria and other potential toxins, trihalomethane and haloacetic acid byproducts are generated that may harm humans after consumption as well. A reliable manner of measuring such drinking water supplies for such trihalomethane and/or haloacetic acids at locations far from the source and closer to dispensers is highly desirable. The CMS-FIA analysis method of the invention has been found to be nearly as reliable as source measuring methods for the same purpose, but with the versatility to measure for such trihalomethane and haloacetic acid contaminants anywhere along the drinking water supply line.

2 Claims, 4 Drawing Sheets

US 7,987,701 B2

REAL-TIME, ON-LINE ANALYSIS FOR THE QUANTIFICATION OF TOTAL HALOACETIC ACID AND TRIHALOMETHANE SPECIES IN DRINKING WATER SUPPLIES

FIELD OF THE INVENTION

The present invention relates to capillary membrane sampling-flow injection analyzer (CMS-FIA) studies of drinking water samples for quantity measurements and species identification of trihalomethane and haloacetic acid contaminants therein. With the necessity to chlorinate drinking water to remove harmful bacteria and other potential toxins, trihalomethane and haloacetic acid byproducts are generated that may harm humans after consumption as well due to suspected carcinogenicity. A reliable manner of measuring such drinking water supplies for such trihalomethane and/or haloacetic acids at locations far from the source and closer to dispensers is highly desirable. The CMS-FIA method of the invention has been found to be nearly as reliable as source measuring methods for the same purpose, but with the versatility to measure for such trihalomethane and haloacetic acid contaminants anywhere along the drinking water supply line.

BACKGROUND OF THE INVENTION

Drinking water has been, and continues to be, heavily treated for bacteria and other microscopic organisms that may cause infection in humans and other animals subsequent to consumption. In order to disinfect water supplies, halogenated materials have been introduced therein that have proven more than adequate for such a purpose. Unfortunately, although such halogenated compounds (chlorinated and chlorinated types, primarily) exhibit excellent disinfection capabilities, when present within aqueous environments at certain pH levels these halogenated compounds may generate byproducts that may themselves create health concerns. The United States Environmental Protection Agency (USEPA) in fact currently regulates four types of trihalomethanes (THM4) and five specific types of haloacetic acids (HAA5) within drinking water. These THM4 are chloroform, bromoform, dibromochloromethane, and bromodichloromethane, and these HAA5 are monochloroacetic acid, dichloroacetic acid, trichloroacetic acid, monobromoacetic acid, and dibromoacetic acid. Removal of such compounds from drinking water is not possible as for typical chlorinated disinfecting compounds, at least not at the same reliability level as for the disinfecting agents (the brominated species listed above may occur as the result of certain chlorinated acids and/or ions reacting with brominated compounds present within the drinking water prior to disinfection or hypobromous acid). Thus, residual amounts may remain within treated water supplies that may require further removal processes to be undertaken. Of course, if the level of contamination is sufficiently low, initiation of such potentially expensive removal steps would be unwise from an economic perspective.

The USEPA currently has set a maximum contaminant level for these THM4 in drinking water at 0.080 mg/L and for these HAA5 in drinking water at 0.060 mg/L (four other haloacetic acids are currently not regulated by the USEPA, bromochloroacetic acid, bromodichloroacetic acid, dibromochloroacetic acid, and tribromoacetic acid; including these, the total haloacetic acid group is known as HAA9). It is thus important to reliably analyze and measure the total amount of such contaminants in order to determine if removal if necessary. The USEPA has instituted its own testing methods for such a purpose. Four such methods are currently in practice to measure HAA5 levels: USEPA 552 and 552.2, which involve the liquid-liquid extraction of haloacetic acids from water sources into methyl-t-butyl ether, followed by derivatization with acidic methanol to form the corresponding haloacetic acid methyl esters. Analysis by gas chromatography-electron capture detection provides reliable measurements of the haloacetic acid amounts present within the subject water supply. The USEPA 552.1 test protocol employs ion-exchange liquid solid extraction, subsequent derivatization into methyl esters, and similar gas chromatography-electron capture detection. The other, USEPA 552.3, is a derivative of the first with optimizations of acidic methanol neutralization procedures for improvement in recoveries for brominated trihalogenated haloacetic acid species. However, these general processes have been found to have numerous drawbacks. For instance, injection port temperature can affect debromination of certain haloacetic acid species (particularly tribrominated types) that may lead to underrepresentation of the amount of such contaminants present within the tested water source. Likewise the water content of the methyl-t-butyl ether extract may dicarboxylate the haloacetic acids, again leading to an underreporting of the actual amounts present within the test sample. Furthermore, the involved processing needed to actually undergo such analysis makes an on-line protocol rather difficult to implement, particularly when hourly sampling is necessary. Other derivatization methods have been either followed or suggested for gas chromatography analyses of drinking water sources as well, including utilizing diazomethane, acidic ethanol, and aniline. Such reactant-based measurements, however, all suffer the same time and labor-intensive problems as with the two USEPA test procedures noted above. As such, on-line analysis through these protocols are difficult, expensive, and labor intensive to implement and run.

Measurement at the source (i.e., within a water purification plant location) may be effective for system-wide average readings; however, in the large supplies of water at such locations, the chances of proper sampling to that effect may be suspect since the contaminants may be present in varied locations, rather than homogeneously mixed throughout the tested water supply itself. Additionally, testing may not uncover the actual level of residual THM4 and/or HAA5 disinfection byproducts prior to the water supply being disbursed to distant dispense sites (transfer pipes, homes, schools, businesses, etc.). In any event, there is a relatively new rule in place that requires utilities to provide evidence of compliance with trihalomethane or haloacetic acid levels at multiple locations, rather than a straightforward system-wide average. Thus, since the above-described derivatization procedures with gas chromatography-electron capture detection analytical methods are not suitable for a uniform trihalomethane/haloacetic acid measurement scheme. There is thus a drive to implement remote testing via real-time, on-line methods for in water supply HAA5, and, more importantly, for HAA9 contaminant level measurements, in addition to the THM4 contaminant levels as well.

Such a desirable on-line procedure has been difficult to achieve, however, particularly as it pertains to the determination of not only the total amount of THM4 and HAA9 within water supplies, but also the amount of each species of THM4 and HAA9 groups present within the tested water source. High performance liquid chromatography, utilizing electrospray ionization-mass spectrometry or ultraviolet absorbance for detection, has been attempted, as well as ion chromatography, with membrane-suppressed conductivity detection or ultraviolet absorbance detection. Other attempts with inductively coupled plasma-mass spectrometry and electrospray ionization-mass spectrometry coupled with ion chromatography have been attempted for this same purpose. The detection level can be as low as 0.5 to less than 10 µg/L for HAA9 species, but only subsequent to sample preparations. The sensitivity and selectivity of ion chromatography and high performance liquid chromatography methods are negatively affected without the cumbersome sample preparations in place, therefore requiring operator intervention during analysis. Again, this issue leads to serious drawbacks when on-line implementation is attempted as well.

Another methodology that has proven effective is post-column reaction-ion chromatography. This has shown promise, but only in terms of quantifying bromate ion concentrations in drinking water samples at a single µg/L level. This dual selectivity form (separation by ion chromatography column as well as the selective reaction with the post-column reagent with the analyte) offers an advantageous test method over the others noted above, except for the presence of more common anions, specifically chloride, at much higher concentrations within the sampled drinking water supply (mg/L instead of µg/L). It was then undertaken to combine the separation capabilities of ion chromatography with the reaction of the haloacetic acid species with nicotinamide, followed by fluorescence detection to measure the individual and total HAA5 concentrations in drinking water at the single µg/L level. The problem with such a protocol, unfortunately, was that bromochloroacetic acid interfered with dichloro- and dibromo-acetic acid quantifications. Despite this problematic limitation, it was determined that fluorescence detection provided a much-improved detection protocol in comparison with ultraviolet and mass spectrometry possibilities. Thus, although such a fluorescence method of detection, coupled with the post-column reaction (again with nicotinamide reagent) and ion chromatography, exhibited the best results in terms of an on-line test method for HAA5 drinking water contaminant measurement levels, there remained a definite need for improvements in total trihalomethane and haloacetic acid measurements and identifications within such test samples. To date, however, there has not been an analytical test protocol that has permitted implementation of such a system within an on-line, real-time monitoring procedure with an acceptable degree of reliability. An automated system that provides such versatility and reliability has simply not been forthcoming within the pertinent art.

ADVANTAGES AND SUMMARY OF THE INVENTION

Accordingly, it is an advantage of the present invention to provide a reliable on-line drinking water analytical protocol for determining the total measurements for both the four different trihalomethanes and nine different haloacetic acids that are commonly present as disinfection byproducts within such water sources. It is an additional advantage of the invention to provide reliability similar to that exhibited by USEPA 552 test method series described above, but at any location along a drinking water supply line and without need for operator involvement.

Accordingly, the instant invention encompasses a method of analyzing drinking water samples comprising the steps of:
 a) providing at least one stream of drinking water that has been disinfected with chlorinated or chlorinated materials;
 b) transporting said at least one stream of drinking water through a capillary membrane sampling device such that all volatile trihalomethane compounds present within said drinking water stream separates from said stream within said capillary membrane sampling device into a stream of reagent water, and wherein any haloacetic acid compounds will remain within said at least one stream of drinking water;
 c) transporting both of said trihalomethane-containing stream of reagent water and said drinking water haloacetic acid-containing stream to a ten-port valve, wherein said valve is configured to inject only one of said trihalomethane-containing stream or said haloacetic acid-containing stream to a mixing manifold at a time, wherein when one of said streams is injected into said mixing manifold, the other stream loads into a sample loop, and wherein said valve alternates from injection to load positions for both streams by action of an actuator;
 d) mixing either of said streams with a fluorescing compound within said mixing manifold to form a fluorescing stream therein; and
 e) transporting the fluorescing stream to a fluorescence detector to determine the amount of each compound within each stream through fluorescence detection. This invention also encompasses a drinking water analytical instrument comprising of a capillary membrane sampling device attached to a ten-port valve which is attached to a mixing manifold which is attached to a fluorescence detector. The ten-port valve permits alternating injections of different streams of drinking water subsequent to separation of volatile compounds from the drinking water stream within the capillary membrane sampling device. As noted above, such a method permits quantification of both total trihalomethane and haloacetic acid species within the subject drinking water sample to determine the potential harmful levels of such suspect carcinogenic compounds therein. The method and the entire instrument may be operated from and at remotely without human operator involvement, at any location along a drinking water supply line.

Such methods have permitted implementation of remote automatic testing procedures and instrumentation along any location of a drinking water supply line. As noted above, the previous analytical approaches suffered from necessary operator involvement, deleterious effects from reactants or simultaneously formed byproducts thwarting reliable measurements from being taken to ensure compliance with federal regulations. This present method and entire analytical instrument has overcome such limitations through the inclusion of a ten-port valve after separation of volatile trihalomethanes from haloacetic acids via CMS and with further refinement of a fluorescing step, all coupled with a remote detection process. The instrumentation does not require human operator involvement unless a breakdown or energy source failure occurs; for testing purpose, however, the analyses can be performed at regular intervals through computer processor control.

DETAILED DESCRIPTION OF THE DRAWINGS AND PREFERRED EMBODIMENTS OF THE INVENTION

Figure 1:
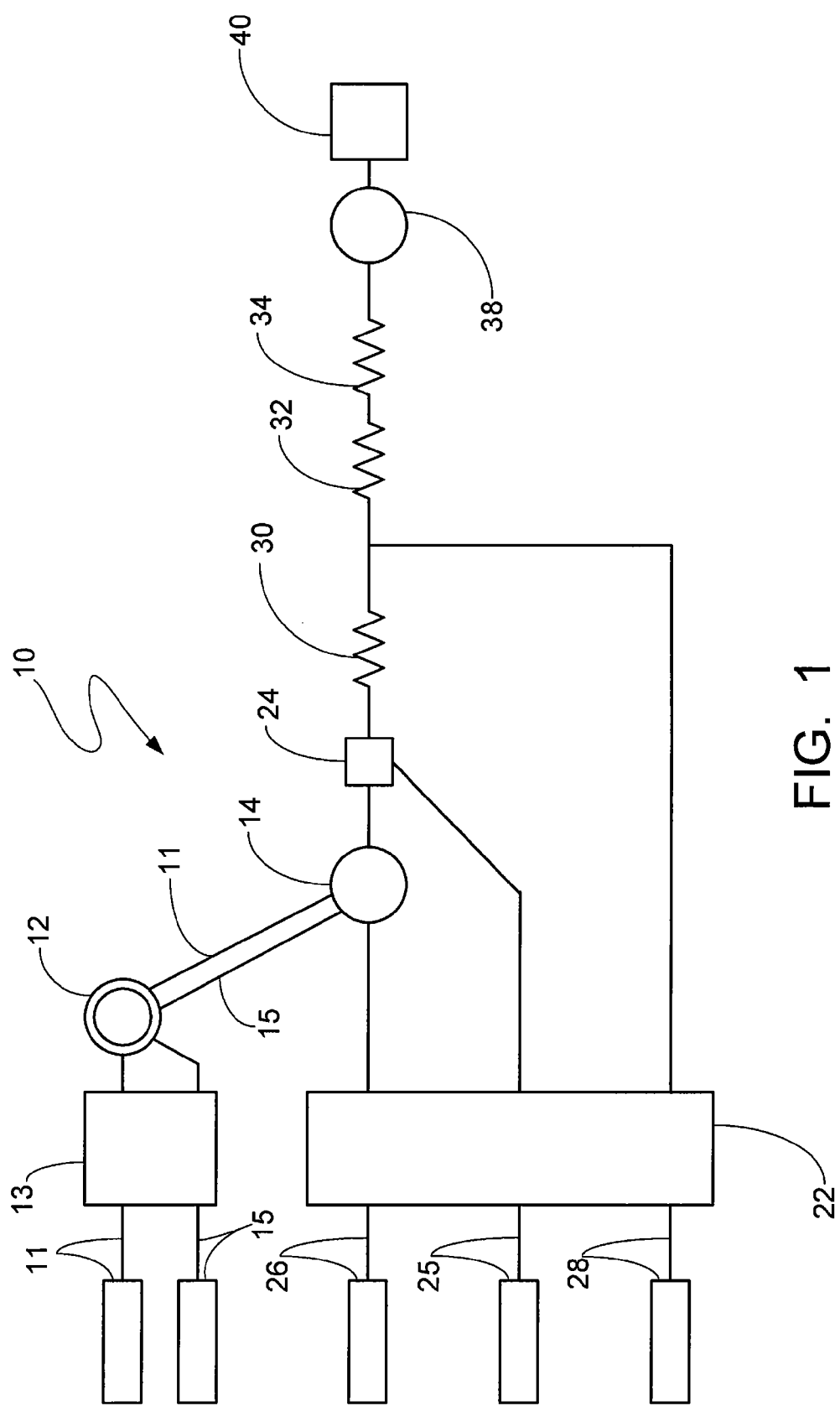
FIG. 1 depicts a broad schematic of the CMS-FIA analyzer utilized for the on-line inventive total THM4 and HAA9 measurement and identification procedure.

As shown in FIG. 1, the overall system basically includes an FIA flow injection analyzer 10 (here a modified FIA Lab 2000) with a capillary membrane sampling device 12 that initially separates the volatile trihalomethanes into a separate stream of water (purified reagent water) 15 from the drinking water sample stream (that retains the non-volatile haloacetic acids therein). The initial drinking water sample is supplied through a line 11 that is transported by a pump 13 (any type of pump may be utilized, although a peristaltic pump commonly associated with the FIA Lab 2000 system is preferred for this purpose) at any desired rate, although preferably, for suitable test purposes, the water sample flows at a rate of 1.0 mL/minute through the pump 13. The sampling component 12 then transports the two different streams of halogenated byproducts to an electrostatically actuated ten-port sample injection valve 14 (more fully described in FIGS. 3 and 4, below) fitted with two water injection sample loops (illustrated as 212 and 214 in FIGS. 3 and 4). This valve 12 is fully automated using a software package (such as Peak Simple from SRI Instruments Inc.) and a single channel serial port data acquisition system 14 (such as Model 203, also from SRI)(this acquisition system also collects the data from fluorescence detectors, such as Model 420 from Waters Inc.)(any suitable automating software and data acquisition systems may be utilized for these purposes). The valve 14 permits alternating injection of either stream into a stream of NaOH (or comparable base solution) carrier 26 for delivery into a mixing manifold 24. This NaOH stream 26 (preferably, though not necessarily 3M in concentration) aids in delivering the sample water stream (of either trihlomethanes or haloacetic acids) to the mixing manifold and ultimately aids in reducing the presence of other potential contaminants within the tested water stream through reaction therewith, as well as increases the eventual intensity of the fluorescing compounds to be detected. Within the mixing manifold 24 is then introduced a stream of sodium thiosulfate 25 (preferably, though not necessarily 0.5% aqueous solution thereof; and alternative chlorine masking agents could be used) to also aid in reducing unwanted interferents (such as hypochlorous acid, hypochlorite ion, etc.) within the two test streams. After mixing all three components (sodium hydroxide, sodium thiosulfate, and test water stream) within a reactor coil 30 (of any type, although preferably such a coil is made from polymeric material and has an outer diameter of about 1.6 mm, an inner diameter of 0.5 mm, and a length of about 2 meters), the resultant solution is then further reacted with a nicotinamide solution (preferably, though not necessarily, a 30% aqueous solution thereof) 28. All three reactants may be delivered for mixing with the test streams through separate pumps, one pump for all three, or even the same pump as the water samples themselves. In this schematic, one pump 22 is utilized for all three reactants. Any flow rate may be set for the introduction of such reactants, although it is preferable that the NaOH is set at a flow rate of about 0.9 mL/minute, and both the sodium thiosulfate and nicotinamide at a flow rate of about 0.6 mL/minute. These three-reactant plus water stream mixture is combined within a second reactor coil 32 (that is preferably fitted with a heating knitted open tubular coil of outer diameter 1.6 mm, inner diameter 0.75 mm, and a length of 10000 mm though the length and type of reactor coil can vary) that is heated to a preferable temperature of about 97° C. (in actuality, any temperature will be suitable for this device, although the higher the temperature the faster the result). The transport rate remained static and the resultant fluorescing solution was then cooled to reduce any bubbles that might form within the resultant stream (preferably, an ice bath is utilized) within the third reactor coil 34 and to maximize fluorescent intensity therein. From there, the resultant solution was then introduced within the fluorescent detector 38. Such a detector 38 then analyzes the different fluorescing THM4 or HAA9 compounds depending upon which stream is currently allowed delivery via the ten-port valve 14. With calibration curves in place, determinations of THM4 and HAA9 compound quantities within the initial drinking water sample are then made. The samples are then ejected out of the detector 38 into a waste receptacle 40.

Figure 2:
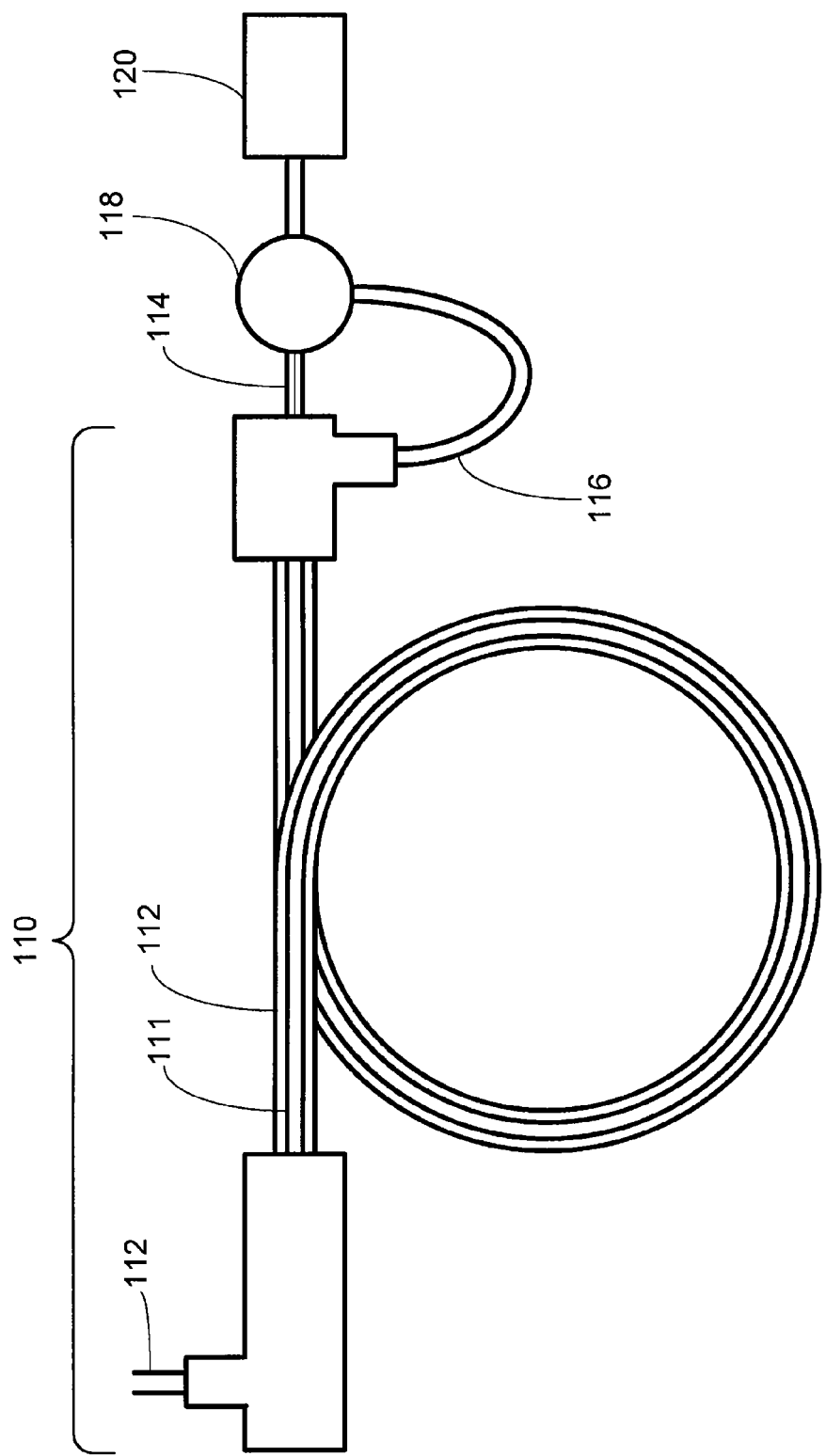
FIG. 2 depicts a closer view of the CMS device of FIG. 1.

In FIG. 2, the capillary membrane sampling component 110 is shown wherein the individual trihalomethanes are fully separated from the haloacetic acids within the drinking water sample stream 112. The CMS 110 includes two feed lines, one being a smaller silicone membrane tubing 111 (from Dow Corning, for example) that fits inside the larger feed line 113 that is made from an inert material (such as TEFZEL®, from Valco Instruments). The silicone membrane tubing 111 is permeable to the volatile trihalomethanes but not to the haloacetic acids. As such, upon introduction of the drinking water samples 112 therein, separation of these two different types of halogenated contaminants occurs readily and nearly completely (if not completely). The silicone membrane tubing 111 includes a stream of purified reagent water (or possibly carrier solutions) into which the trihalomethane are dissolved upon permeation through the membrane 111. Thus, two streams are formed; one with haloacetic acids and the remaining drinking water sample, and the other the trihalomethanes and reagent water. Upon separation, the samples are then passed in separate streams 114, 116 to the ten-port valve 118 and eventually, and still separately, to the flow injection analyzer 120 for further analysis.

Figure 3:
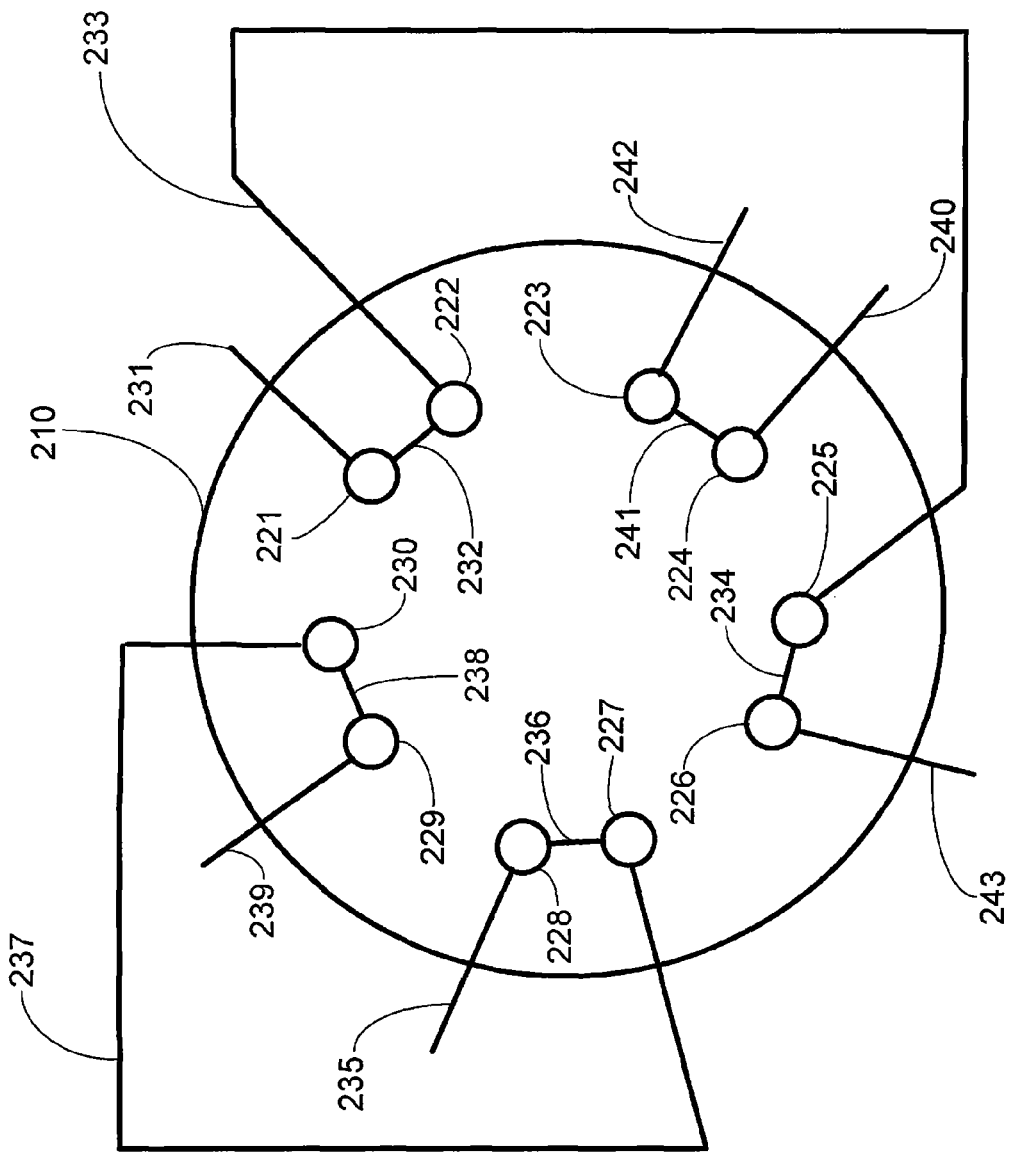
FIG. 3 depicts the ten-port valve of FIG. 1 in closer view.
Figure 4:
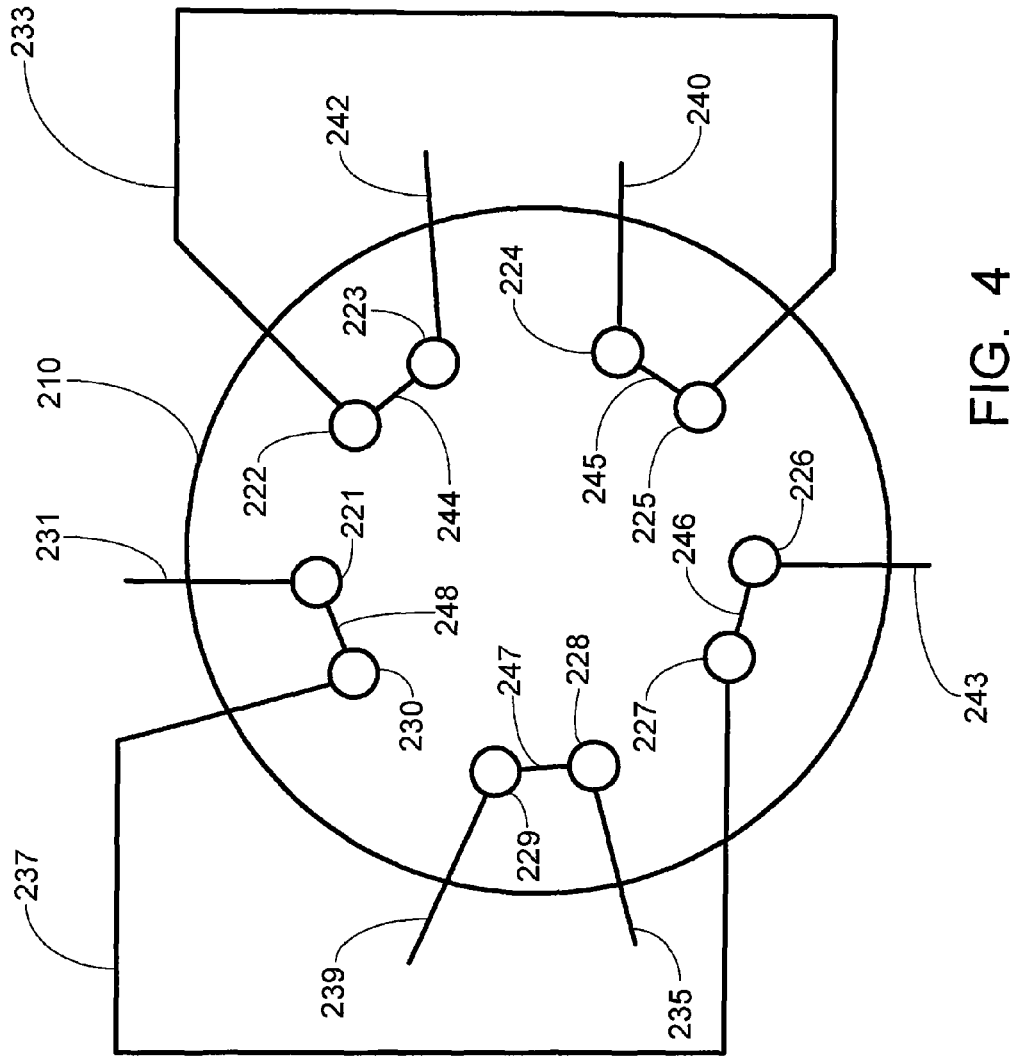
FIG. 4 depicts a different alternate position of the ten-port valve of FIG. 3.

In FIG. 3, the ten-port valve (12 of FIG. 1) is shown in greater detail and in relation to introducing the separate THM4 and HAA9 streams into a sodium hydroxide carrier for further delivery to the mixing manifold (24 of FIG. 1). This valve 210 includes, as the name suggests, 10 individual ports 221, 222, 223, 224, 225, 226, 227, 228, 229, and 230. These ports 221 through 230 are configured to alternate target delivery ports by utilization of a non-illustrated disk. Such a disk will either allow transport from one port to another or cut off the supply and allow for movement from and/or to another port instead. Thus, in FIGS. 3 and 4, the first port 221 always delivers an NaOH carrier stream via a first line 231 into the valve 210 and the sixth port 226 always delivers the NaOH carrier into a mixing manifold (24 in FIG. 1) via a last line 243. The NaOH carrier stream will either deliver with it to the sixth port 226 and last line 243 a sample of trihalomethane-containing water or haloacetic acid-containing water, depending on the position in which the valve 210 is configured through an actuator (not illustrated). In FIG. 3, the second port 222 receives the NaOH stream from the first port 221 through a second line 232 and delivers the NaOH carrier stream through a HAA9 loop line 233 to a fifth port 225 and on to said sixth port 226 through an internal fourth line 234, and then to said last line 243 (and further then to the mixing manifold 24 of FIG. 1). In this configuration, the trihalomethane-containing water stream is introduced within the valve 210 through the eighth port 228 via the THM4 injection line 235, and is delivered through the valve 210 through the seventh port 227 via a sixth line 236, which delivers the same stream through to the tenth port 230 via a THM4 sample loop line 237 which, in turn, delivers the stream to a ninth port 229 via an eighth line 238, and, finally, to a waste receptacle (not illustrated) via a ninth line 239. Simultaneously, the haloacetic acid-containing water stream is introduced into the valve 210 via a HAA9 injection line 240 into a fourth port 224, which delivers the stream to the third port 223 via an eleventh line 241, and then to a waste receptacle (not illustrated) via a twelfth line 242. During this specific configuration of the valve 210, the trihalomethane-containing water stream is continuously flowing through the THM4 loop line 237 until the valve 210 alternates to the position of FIG. 4, while the haloacetic acid-containing water stream is basically just being delivered to waste. Upon reconfiguring of the arrangement through the aforementioned non-illustrated actuator, the delivery of water streams is basically reversed. At that time, the FIG. 4 arrangement is in place. All the trihalomethane-containing water that was remaining in the THM4 loop line 237 at the moment the actuator reconfigured the valve 210 is then carried by the NaOH stream to the mixing manifold (24 of FIG. 1) and on for the target analyses. At that instant, the THM4 stream then delivers to a waste receptacle (not illustrated) and the HAA9 stream flows continuously through the valve 210 via the HAA9 loop line 233. Upon reconfiguring once again, the HAA9 stream within the loop line 233 will be delivered with the NaOH carrier stream to the mixing manifold (24 of FIG. 1). This will continue in alternating arrangement as long as desired with five different lines 244, 245, 246, 247, 248 redirecting the flow of either the HAA9 stream or THM4 stream in a fashion opposite from the previous configuration. The valve 210 may be made of any type of material, as may the ports 221-230, and the lines 231-243, although polymeric materials (such as polystyrene and polycarbonate, preferably) may be utilized for such a purpose. The lines 231-243 may actually be of any length, with about 30 cm preferable, particularly with the loop lines 233, 237.

In this manner, the THM4 compounds and HAA5 (or HAA9) compounds are separated from each other via CMS, then reacted, fluoresced, and measured through FIA, alternatively (the ten-port valve permitted separation and analysis of the THM4 and HAA9 classes in this manner). Such a system can be implemented at any location and, through automation, does not require continued operator input or control. The peristaltic pumps are controlled through computer software or other type of automation, thereby allowing, again, for remote utilization. Additionally, the entire system may be set up for wireless communication from a remote location to a central location for review of the analytical results. The main issue in terms of proper selectivity of such a system for such a purpose is the reliability thereof at such remote locations. In order to determine the feasibility of such an analytical method, it was first necessary to compare the results thereof to standard USEPA methods.

Two specific methods have been followed by water utilities for compliance measurements, albeit from the water source itself. In terms of such source measurements, however, these standards (USEPA 502.2 and 552.3 test protocols) have been the most reliable. Comparisons of drinking water samples for similar measurements through these compliance standard tests and those of the instant inventive method were undertaken. If the measurements were actually similar in amounts, identifications, and standard deviations, it would be properly assumed that the new method would be significantly reliable to the degree required under Federal regulations.

The USEPA 502.2 method measures for individual and total THM4 as well as other volatile byproducts. This method utilizes a TRACOR® 540 gas chromatography with Hall/PID detectors, a Tracor LSC-2 sample concentrator, and a TEKMAR® 2050 Autosampler. The sample preparations, collections and analyses were performed pursuant to those described within this specific methodology, except that the GC oven was increased in temperature in order to shorten the analysis time necessary for proper THM4 identifications and measurements. The MDLs for the THM4 compounds were 0.4 μg/L each for bromoform and chloroform, 0.6 μg/L each for bromodichloromethane and dibromochloromethane; the mean percent recoveries for these species were 96.7%, 101%, 98.6%, and 98.6%, respectively. The relative standard deviations for this method were 4.9%, 4.6%, 6.5%, and 6.4%, respectively, as well.

The USEPA Method 552.3 measures HAA9 concentrations in drinking water only. As noted above, liquid-liquid extraction was undertaken into methyl-t-butyl ether, followed by derivatization of the resultant compounds with acidic methanol into methyl esters of the HAA9 compounds. These compounds were then analyzed via GC-ECD wherein the GC was a VARIAN® 3380 equipped with a Ni-63 ECD detector. The MDL values for the HAA9 compounds were, respectively for monochloroacetic acid (MCAA), dichloroacetic acid (DCAA), trichloroacetic acid (TCAA), monobromoacetic acid (MBAA), dibromoacetic acid (DBAA), bromochloroacetic acid (BCAA), bromodichloroacetic acid (BDCAA), dibromochloroacetic acid (DBCAA), and tribromoacetic acid (TBAA), were (in μg/L) 0.3, 0.2, 0.2, 0.1, 0.4, 0.2, 0.3, 0.4, and 0.5. The mean recoveries were, respectively, (in percentages) 119, 117, 64.5, 161, 89.5, 76.9, 101, 93.1, and 94.1. Also, the relative standard deviation values were, again, respectively, (in percentages) 2.1, 1.0, 2.3, 0.6, 3.5, 3.5, 2.9, 3.5, and 4.6.

Thus, as noted above, it was important that the system devised exhibit similar results for these measurements. However, optimization of the separation capabilities and collection of only the compounds for which measurement and identification were necessary was required initially. Fluorescent intensity needed to be improved to the level that detection would permit effective measurements. The sodium hydroxide carrier stream was of great criticality in increasing this intensity. The preferred 3M NaOH was thus determined to meet this requirement. Additionally, the potential presence of certain other halogenated disinfecting compounds (most notably hypochlorous acid, hypochlorite ions, and chloramines) could be problematic as such species may interfere with the detection of the other types of compounds within the FIA. As such, it was important to provide a capillary membrane sampling device that would selectively exclude any such species. The permeation of such species was prevented, or at least reduced to the level that any such species that did permeate the subject membrane would not interfere with the THM4 measurements. In terms of the HAA9 compounds, these other species would interfere with those measurements, generally, at any concentration, apparently. As such, it was important to select a masking reagent as it concerned such interfering species. Thus, sodium thiosulfate (or equivalent dechlorinating agent) was required to be introduced within the overall system to downgrade any interference these species would potentially create in terms of the measurements of HAA9 compounds within the overall analytical instrument. At a 0.5% sodium thiosulfate aqueous concentration, and at a pH of 4.5, there would be no detection of hypochlorous acid, hypochlorite, or mono- or di-chloramines at concentrations normally detected in drinking water samples (from about 1 to 5 mg/L).

Thus, after such optimization was put in place, drinking samples were then tested in accordance with the device described supra. Initial standard samples of THM4 and HAA5 were injected therein (100 μg/L concentrations) followed by several deionized (reagent) water samples to clean out the system (this reagent water blank sample was tested for 3 hours, every 45 minutes therein, to determine if any residual effect problems would exist after such intervals of time had passed between tests. It was found that after one hour the amount of residual THM4 and/or HAA5 remaining within the overall system was de minimis and would not affect any further testing results. Thus, at least from this standpoint, uniform hourly, interval analyses would be possible.

Initial standards of different concentrations were then prepared of the THM4 and HAA5 compounds in order to generate calibration curves thereof. As is customary, the peak height of the FIA gradient of total THM4 and total HAA5 was plotted as a function of concentration. In terms of these initial calibration studies, the MDLs of each compound were very promising in comparison with those of the US EPA Test Methods 502.2 and 552.3, undertaken and described above MDL for the THM4 was 2.5 µg/L, the mean recovery was 108%, and the standard deviation value was 4.0%; for the HAA5, the MDL was 3.3 µg/L, mean recovery was 102%, and relative standard deviation value was 3.5%. The calibration curves thus provided an acceptable measuring stick with which to plot the concentrations of the actual unknown drinking water sample values for the THM4 and HAA5 compounds.

Within both chlorinated and chlorinated treated water systems, samples were drawn and tested within the inventive system, the 502.2 test method, and the 552.3 test method. For the chlorinated water samples, the testing was performed over a 131 hour period; for the chlorinated, a 71 hour time period. Concentrations of THM4 and HAA9 were monitored at a rate of 1 sample per hour (with every $12^{th}$ hour excluded in order to run a standard control) through the inventive analyzer; for each USEPA method, for the first two days of sampling, measurements were taken every hour, followed by one sample every two hours thereafter. From 79 comparisons made, the resultant average concentrations and standard deviation measurements were, respectively, in chlorinated water samples, for 502.2, 1.9 and 0.7 µg/L (with a concentration range of 0.7 to 4.1 µg/L), and, for the inventive system, 2.1 and 0.9 µg/L (with a concentration range of 0.2 to 5.3 µg/L). Assuming that the 502.2 test method provided the "true value" of the level of contaminants (here THM4), a bias was calculated as a comparison therewith the 502.2 results, being the inventive results minus each individual 502.2 test method result. The average bias was 0.2 µg/L, with a standard deviation value of 1.1 µg/L, and a bias range of from −2.3 to +3.1 µg/L. For the chlorinated water samples, the number of analyses for 502.2 and the inventive were both 52, average concentrations were 53.5 and 48.2 µg/L, respectively, standard deviation ranges were 4.1 and 3.4 µg/L, respectively, with the 502.2 concentration range of 45.6 to 62.0 µg/L, and the inventive concentration range from 41.8 to 56.1 µg/L. As above, the average bias was calculated and determined to be −5.3 µg/L, with a standard deviation of 3.7 µg/L, and a bias range of −11.4 to 4.2 µg/L. Although a greater range of bias was determined, the results were still quite similar as for the chlorinated water samples, which were very similar in measurements.

The HAA9 levels were then measured and analyzed in comparison with the 552.3 test method. The same time lengths were followed as above, as was the every $12^{th}$ hour control check. For the chlorinated water samples, 83 comparisons were made between the inventive and 552.3 test method, with, for 552.3, an average concentration of 3.0 µg/L (compared with 2.3 µg/L for the inventive), and a standard deviation concentration of 0.8 (compared with the inventive value of 1.2 µg/L), at a concentration range of 1.9 to 7.6 µg/L (as compared with the inventive range of 0.6 to 6.3 µg/L). As above, the average bias was calculated; this was found to be −0.7 µg/L, with a standard deviation of 1.4, and a bias range of −6.0 to 3.3 µg/L. These were excellent results. For the chlorinated water samples, 44 comparisons were made with, for 552.3, an average concentration of 77.1 µg/L, and a standard deviation of concentration of 3.7 µg/L (at a concentration range of 68.6 to 83.2 µg/L). The inventive CMS-FIA system generated an average concentration of 50.9 µg/L at a standard deviation of 2.9 µg/L and a concentration range of 44.2 to 54.6 µg/L. The average bias was −26.2 µg/L, with a standard deviation of 3.9 µg/L and a bias range of −33.5 to −15.1 µg/L. Such results were rather disparate.

The THM4 measurements, above, thus show, with a slightly positive bias on average, that the inventive method reported higher concentrations than the USEPA 502.2 method. Considering the possibility of other halogenated compounds permeating the membrane of the capillary membrane sampling device, these results would not be out of the question. Furthermore, the larger negative bias results for the 552.3 test method comparisons are expected as this USEPA test protocol requires storage of water samples after addition of ammonium chloride crystals thereto. After time, these crystals would undoubtedly react with other types of halogenated compounds within the water sample to generate larger concentrations of HAA9 compounds therein. As such, the resultant negative bias levels most likely show that the on-line system (real-time in effect) of the CMS-FIA inventive analytical method provides a more reliable measuring procedure than, or, at least, a comparable method to, the Federal regulatory compliance standards.

The preceding examples are set forth to illustrate the principles of the invention, and specific embodiments of operation of the invention. The examples are not intended to limit the scope of the method. Additional embodiments and advantages within the scope of the claimed invention will be apparent to one of ordinary skill in the art.

What we claim is:

1. A method of analyzing drinking water samples comprising the steps of:
    a) providing at least one stream of drinking water that has been disinfected with chlorinated or chloraminated materials;
    b) transporting said at least one stream of drinking water through a capillary membrane sampling device such that all volatile trihalomethane compounds present within said drinking water stream separates from said stream within said capillary membrane sampling device into a stream of reagent water, and wherein any haloacetic acid compounds remain within said at least one stream of drinking water;
    c) transporting both of said trihalomethane-containing stream of reagent water and said drinking water haloacetic acid-containing stream to a ten-port valve, wherein said valve is configured to inject only one of said trihalomethane-containing stream or said haloacetic acid-containing stream to a mixing manifold at a time, wherein when one of said streams is injected into said mixing manifold, the other stream loads into a sample loop, and wherein said valve alternates from injection to load positions for both streams by action of an actuator;
    d) mixing either of said streams with a fluorescing compound within said mixing manifold to form a fluorescing stream therein; and
    e) transporting the fluorescing stream to a fluorescing detector to determine the amount of each compound within each stream through fluorescence detection.

2. A drinking water analytical instrument comprising a capillary membrane sampling device including two separate streams leading therefrom and attached separately to a ten-port valve, said ten-port valve attached to a mixing manifold which is attached to a fluorescence detector.

* * * * *